United States Patent [19]

Hashim

[11] 4,230,696
[45] Oct. 28, 1980

[54] POLYPEPTIDES USEFUL FOR THE PURPOSE OF TREATING MULTIPLE SCLEROSIS

[75] Inventor: George A. Hashim, Irvington, N.Y.

[73] Assignee: St. Luke's Hospital, New York, N.Y.

[21] Appl. No.: 941,001

[22] Filed: Sep. 11, 1978

Related U.S. Application Data

[63] Continuation-in-part of Ser. No. 648,379, Jan. 12, 1976, Pat. No. 4,113,858, which is a continuation-in-part of Ser. No. 542,175, Jan. 20, 1975, abandoned, which is a continuation-in-part of Ser. No. 315,140, Dec. 12, 1972, Pat. No. 3,864,481.

[51] Int. Cl.$^3$ .................... A61K 37/00; C07C 103/52
[52] U.S. Cl. .............................. 424/177; 260/112.5 R
[58] Field of Search ................. 260/112.5 R; 424/177

[56] References Cited

U.S. PATENT DOCUMENTS

| 3,864,481 | 2/1975 | Hashim | 260/112.5 R |
| 4,113,858 | 9/1978 | Hashim | 260/112.5 R |

OTHER PUBLICATIONS

Pettit, Synthetic Peptides 1, 1971, pp. 104 & 105.

*Primary Examiner*—Delbert R. Phillips
*Attorney, Agent, or Firm*—Kane, Dalsimer, Kane, Sullivan and Kurucz

[57] ABSTRACT

Synthetic compounds of the formula:

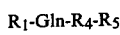

and the acid addition salts thereof are disclosed wherein $R_1$ and $R_5$ are each independently selected from the group consisting of hydrogen, hydroxy, the residue of an amino acid and the residue of a polypeptide and $R_4$ is selected from the group consisting of lysine and arginine residues; provided that $R_1$ and $R_5$ are not both hydrogen or both hydroxyl at the same time. The disclosure is also of intermediate compounds for preparing the compounds of the above formula and derivative compounds having the same biological activity.

Disclosed also are pharmaceutical compositions wherein the essential active ingredient is a synthetic compound of the invention. The compounds and compositions of the invention are useful for the prevention, suppression, treatment and diagnosis of multiple sclerosis.

28 Claims, No Drawings

POLYPEPTIDES USEFUL FOR THE PURPOSE OF TREATING MULTIPLE SCLEROSIS

CROSS-REFERENCE TO RELATED APPLICATIONS

This application is a continuation-in-part of copending application Ser. No. 648,379 filed Jan. 12, 1976 issued as U.S. Pat. No. 4,113,858 and which in turn was a continuation-in-part of U.S. application Ser. No. 542,175 filed Jan. 20, 1975, now abandoned, which in turn was a continuation-in-part of application Ser. No. 315,140 filed Dec. 12, 1972 and which is now U.S. Pat. No. 3,864,481.

BACKGROUND OF THE INVENTION

1. Field of the Invention

The invention concerns novel synthetic polypeptides useful in the diagnosis and treatment of multiple sclerosis; intermediates and derivatives thereof.

2. Brief Description of the Prior Art

It has been reported that the basic protein isolated from myelin of the central nervous system of man and animals induces experimental allergic encephalomyelitis (EAE), an auto-immune disease of the central nervous system. The structure for the basic protein was published by E. H. Eylar, Steven Brostoff, George Hashim, Juanita Caccam, and Paul Burnett entitled "Basic Al Protein of the Myeline Membrane", The Journal of Biological Chemistry, Vol. 246, No. 18, Issue of Sept. 25, 1971, pp. 5770–5784. Also, it has been shown that the disease inducing basic protein is readily hydrolyzed by proteolytic enzymes. It is also known that there is more than one disease inducing region found on the native basic protein molecule. These regions have been isolated in the form of peptides following hydrolysis of the basic protein. The essential requirement for disease induction in the guinea pig is the linear sequence of at least nine amino acid residues having the schematic formula:

H—Phe—Ser—Trp—Gly—Ala—Glu—Gly—Gln—Lys—OH

For convenience, the amino acid groups in the above formula, and at times hereinafter, are referred to by abbreviations, following accepted and common practice in peptide chemistry. For example, the following abbreviations for amino acids are used, at times, throughout the following specification and claims:

Lys—lysine
His—histidine
Arg—arginine
Thr—threonine
Ser—serine
Glu—glutamic acid
Pro—proline
Gln—glutamine
Gly—glycine
Ala—alanine
Leu—leucine
Ileu—isoleucine
Tyr—tyrosine
Trp—tryptophan
Phe—phenylalanine In each instance herein, it should be understood that in referring to amino acids, both the D- and L-isomeric forms are intended to be identified unless otherwise indicated.

For disease induction of guinea pigs the linear sequence of amino acid residues required is of the schematic formula:

H—Phe—Ser—Trp—Gly—Ala—Glu—Gly—Gln—Arg—OH and for disease induction in monkeys and rabbits the linear sequence of amino acid residues required is of the schematic formula:

H—Thr—Thr—His—Tyr—Gly—Ser—Leu—Pro—Gln—Lys—OH.

Investigators have shown that EAE can be induced in animals by administering a natural compound having one of the disease inducing regions of the basic proteins. Other disease inducing peptides produced from the native basic protein by hydrolysis have been isolated. The disease induced by the active regions has the same clinical and pathological manifestations as that produced when the whole protein is administered.

Unexpectedly, the administration to a mammal of the synthetic compounds of my invention does not induce disease in the mammals as occurs upon adminstration of the naturally occurring analogs.

SUMMARY OF THE INVENTION

The invention comprises synthetic compounds of the formula:

$$R_1\text{—Gln—}R_4\text{—}R_5 \qquad (I)$$

wherein $R_1$ and $R_5$ are each independently selected from the group consisting of hydrogen, hydroxy, the residue of an amino acid and the residue of a polypeptide and $R_4$ is selected from the group consisting of the residues of lysine and arginine; provided that $R_1$ and $R_5$ are not both hydroxyl or both hydrogen at the same time.

Preferred compounds (I) are those wherein $R_4$ is a residue of lysine. Within the scope of the formula (I) are compounds of the formula:

$$H\text{—}(A)\text{—}(B)_x\text{—OH} \qquad (I\text{-}A)$$

and the acid addition salts thereof,
wherein X is an integer of at least 0; A and B each represent a divalent moiety of the formula:

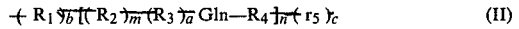 (II)

wherein $R_1$ and $R_5$ are each selected from the group consisting of the residue of an amino acid and the residue of a polypeptide; $R_2$ is selected from the residue of tryptophan and tyrosine; $R_3$ represents the residue of an amino acid; $R_4$ is selected from the residue of lysine and arginine; a is an integer of from 0 to 4, inclusive; b and c are each integers of at least 0; m is an integer of from 0 to 1, inclusive; and n is an integer of at least 1; provided that when $R_1$ is the residue of a polypeptide, b is 1 and when $R_5$ is the residue of a polypeptide, c is 1.

Although theoretically there is no upper limit to the integer value of x, b, c and n, except as hereinbefore provided for, as a practical matter their upper values are limited by the preference and the molecular weight of the compound of formula (I) be less than about 100,000.

Also within the scope of the formula (I) given above are compounds of the formulae:

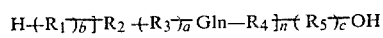  (I-B)

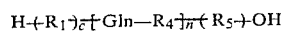  (I-C)

wherein $R_1$, $R_2$, $R_3$, $R_4$, $R_5$, a, b, c and n are previously defined and

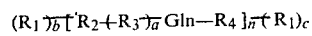  (I-D)

wherein $R_1$, $R_2$, $R_3$, $R_4$, $R_5$, a, b, c and n are as previously defined, provided further $R_1$ is a polypeptide having at least a single amino acid residue.

The invention also comprises a pharmaceutical composition, which comprises; an effective amount for the prevention, suppression, treatment and diagnosis of multiple sclerosis of a compound of the formula (I) above, in admixture with a pharmaceutically acceptable parenteral carrier. Such pharmaceutical compositions include parenterally administrable therapeutic unit dosage forms which comprise from about 0.005 mg to about 1,000 mg. of a synthetic compound of the formula (I) in a milliliter of a pharmaceutically acceptable parenteral carrier.

The synthetic compounds (I) of the invention are useful for inhibiting the induction of experimental allergic encephalomyelitis (EAE) in the test mammals. Experimental allergic encephalomyelitis is the experimental model disease for multiple sclerosis in humans. The synthetic compounds (I) of the invention are non-encephalitogenic when administered in therapeutic dosages to mammals and are useful for the prevention, suppression, treatment and diagnosis of multiple sclerosis in mammals including humans. The administration of therapeutic dosage units of the synthetic compounds (I) will prevent the re-occurrence of encephalomyelitis and suppress in the active stage further deterioration of nervous tissue in mammals including human beings. Such administration to mammals will also prevent the formation of newly sensitized cells and block active sensitized cells from doing damage to nervous tissue.

The term "synthetic compound" is used throughout the specification and claims in its normally accepted sense as meaning a man-made product of chemical synthesis, as opposed to products of nature.

The term "residue of an amino acid" is used herein to mean the divalent moiety obtained upon the removal of the hydroxyl of a carboxyl group and the hydrogen atom from the amino group of an amino acid or the monovalent moiety obtained upon removal of one of said hydroxyl or hydrogen. Illustrative of such as a divalent moiety of formula:

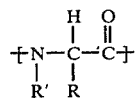  (III)

wherein R, when taken independently, represents hydrocarbyl or hydrocarbyl substituted with an inert group; R' when taken independently is hydrogen; and R and R' when taken together represent the divalent moiety of formula:

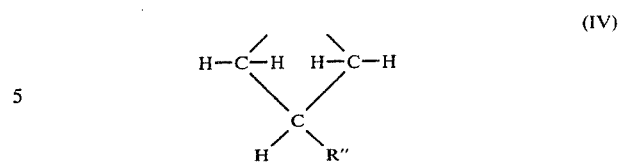  (IV)

wherein R" represents hydrogen or hydroxyl. Illustrative of the monovalent moieties are those of formula:

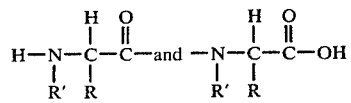

(III-A)        (III-B)

wherein R and R' are as defined above.

The term "hydrocarbyl" as used throughout the specification and claims means that monovalent moiety obtained upon removal of a hydrogen atom from a parent hydrocarbon. Illustrative of hydrocarbyl are alkyl groups such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and isomeric forms thereof; cycloalkyl groups such as cyclopropyl, cyclobutyl, cyclopentyl, cyclohexyl, cycloheptyl, cyclooctyl, 2-methylcyclopentyl, 2,3-dimethylcyclobutyl, 4-methylcyclobutyl, 3-cyclopentyl-propyl and the like; cycloalkenyl groups such as cyclobutenyl, cyclopentenyl, cyclohexenyl, cycloheptenyl, cyclooctenyl and the like, including isomeric forms thereof; cycloalkadienyl groups such as cyclopentadienyl, cyclohexadienyl, cycloheptadienyl and the like; aryl groups such as phenyl, tolyl, xylyl, naphthyl, biphenylyl and the like; aralkyl groups such as benzyl, phenethyl, phenpropyl, naphthmethyl and the like.

The term "hydrocarbyl substituted with an inert group" as used herein means a hydrocarbyl group as defined above wherein one or more hydrogen atoms have been replaced with a group such as hydroxyl, carboxyl, amino, guanidino, mercapto, methylthio,

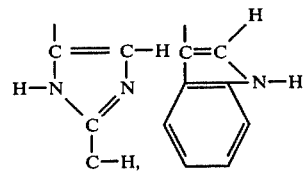

and like groups.

The term "residue of a polypeptide" means the monovalent moiety obtained upon the removal of a hydrogen atom or a hydroxyl group from a polypeptide having within its structural makeup a terminal amino acid group, including di-, tri-, and higher polypeptides.

The term "polypeptide" as used herein includes a protein, recognizing that the latter are by convention generally considered to be polypeptides having a molecular weight over about 10,000 and of a more complex nature being made up of polypeptide chains.

DETAILED DESCRIPTION OF THE INVENTION

The compounds (I) of the invention may be prepared according to conventional and well-known methods of synthesizing polypeptides. Illustrative of those methods which may be employed are the solid phase peptide synthesis procedures described by R. B. Merrifield in the Journal of the American Chemical Society, Vol. 85, p. 2149 (1963); by G. R. Marshall and R. B. Merrifield, Biochemistry, Vol. 4, p. 2394, (1965); and by A. Marglin and R. B. Merrifield, Journal of the American Chemical Society, Vol. 88, p. 5051 (1966). In general, the method comprises starting with the first amino acid desired in the sequence, linked as an ester to a benzyl group on an insoluble polymer such as polystyrene. The alpha-amino group is condensed with a second amino-protected and activated amino acid followed by de-blocking so that the peptide grows on the polymer support.

The resin (polymer support+peptide), in tiny granules, is simply steeped in excess amino acid derivative, then washed, then treated with acid and washed again and the sequence repeated with desired amino acids until the desired amino acid additions and sequences are obtained. Then the resin is treated with stronger acid to remove peptide from the polymer benzyl groups (via $S_N1$ solvolsis at benzyl carbons). Generally, the entire procedure is carried out under an inert atmosphere (nitrogen) and at room temperatures. Completion of each sequence in the overall procedure is readily observed by conventional techniques, i.e.; infrared analysis, thin-layer chromatography and like methods of analysis.

The peptides so prepared generally are recovered in pure forms by conventional techniques such as filtration, recrystallization, counter-current distribution, chromatography and like methods. For complete details of the solid-phase method of peptide synthesis, see Merrifield, supra.

The relatively high molecular weight compounds (I) of the invention, i.e.; those wherein $R_1$ and/or $R_5$ are residues of a polypeptide may also be conveniently prepared by condensing the corresponding compound illustrated by those of formula:

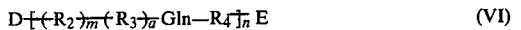  (VI)

wherein $R_2$, $R_3$, $R_4$, a, m and n are as defined above; one of D and E is hydroxyl and the other of D and E is hydrogen; with a polypeptide, including a natural polypeptide such as albumin or gamma globulin. The reaction may be carried out according to the method of Merrifield, supra. The starting compounds (VI) may also be prepared following the procedure of Merrifield, supra.

Those compounds of the formula (I-A) wherein n is greater than 1 or where X is greater than 0 are conveniently prepared by condensation of the appropriate and corresponding compounds (VI) either sequentially or randomly as desired. The method is well known; see for example Hirshmann et al., JACS, 91,507, (1969). Alternatively, such compounds within the scope of the formula (I-A) may be prepared by the random polymerization of the appropriate N-carboxy anhydrides of the corresponding component peptides and amino acids; see for example the methods described in Lorenzi, et al., Biochem. 10, 3046, (1971) and Friedman, et al., JACS, 83, 4050, (1961).

The alpha-amino acids employed to prepare the compounds (I) of the invention are of the general formula:

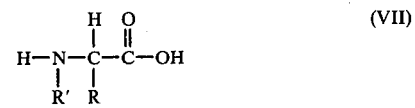  (VII)

wherein R and R' are as previously defined. The amino acids of formula (VII) are a well-known class of compounds prepared by a variety of well-known procedures; for example, by reduction of α-oximino acids (Barry et al., J. Org. Chem., 12, 460 (1947); by hydrolysis of hydanoins (Ware, Chem. Revs. 46, 403, (1950); by reaction of α-halo acids with ammonia (Marvel, Org. Syn., Vol. 20, pg. 106; Vol. 21, pgs. 60 and 74); reductive amination of α-keto acids [Knoop et al., Z. physiol. Chem., 148, 294 (1925) and 170, 186 (1927)]; and from α-amino cyanides by the well-known Strecker synthesis (Allen et al., Org. Syn., Coll. Vol. 3, 275). A review of various α-amino acids and methods of synthesis can be found in the text "Chemistry of the Amino Acids", supra., Chapter 8.

Representative of preferred α-aminoacids employed in preparing preferred compounds (I) are the naturally occuring amino acids such as lysine, histidine, arginine, threonine, serine, glutamic acid, proline, glutamine, glycine, alanine, leucine, isoleucine, tyrosine, tryptophan and phenylalanine. Both the D- and L-stereoisomer forms may be used.

The invention relates also to pharmaceutical dosage unit forms for systemic (parenteral) administration, which are useful for the diagnosis, supression or prevention of multiple sclerosis in mammals. The term "dosage unit form" as used in this specification and in the claims refers to physically discrete units suitable as unitary dosages for mammalian subjects, each unit containing a predetermined quantity of the essential active ingredient, i.e.; a compound (I), calculated to produce the desired effect in combination with the required pharmaceutical means which adapt said ingredient for systemic administration. Examples of dosage unit forms in accordance with this invention are sterile preparations in liquid vehicles for parenteral administration and sterile dry preparations for the extemporaneous preparation of sterile injectable preparations in a liquid vehicle. Carriers or vehicles include vegetable oils, water, ethanol, and polyols, for example, glycerol, propylene glycol, liquid polyethylene glycol, and the like. Liquid pharmaceutical preparations for parenteral administration prepared in water or aqueous solutions advantageously contain suspending agents, such as for example, sodium carboxymethylcellulose and the like. They must be sterile and must be fluid to the extent that easy syringeability exists. Parenteral preparations must also be stable under the conditions of manufacture and storage, and ordinarily contain in addition to the basic solvent or suspending liquid, preservatives in the nature of bactericidal and fungicidal agents, for example, parabens, chlorobutanol, benzyl alcohol, phenol, thimerosal, and the like. In many cases it is preferable to include isotonic agents, for example, sugars or sodium chloride. Any solid preparations for subsequent extemporaneous preparation of sterile injectable preparations are sterilized, preferably by exposure to a sterilizing gas, such as for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.001 mg. to about 1000 mg. of the essential active ingredient [a compound of formula (I)] per dosage unit form. The amount of the essential active ingredient provided in the pharmaceutical dosage unit forms is based on my finding that the effective amount of compounds (I) of the invention, for obtaining the desired therapeutic effect in mammals is within a range from about 0.001 mg. per kg. to about 25 mg. per kg. of body weight of the recipient, daily. Preferably, 0.5 mg./kg. to about 5 mg./kg. daily is provided. The preferred amount for diagnosis of multiple sclerosis is within the range of from about 0.0001 mg. to about 1.0 mg. per kg. of body weight of the recipient mammal.

Any compound of the formula (I) above may be used to obtain a positive diagnosis of multiple sclerosis in mammals, to treat mammals suffering from multiple sclerosis and to prevent multiple sclerosis in mammals. The procedure for their use is described in the parent U.S. Pat. application, Ser. No. 648,379 filed Jan. 12, 1976 (U.S. Pat. No. 4,113,858).

Certain derivative compounds of the compounds (I) of the invention also possess the biological activity associated with the compounds (I) of the invention and are within the scope of the invention. Representative of such derivative compounds are the acylate derivatives, i.e.; compounds where one or more of the hydroxyl, amino and/or imino groups on the molecule of the compound (I) are acylated. Acylation of the hydroxyl, amino or imino groups, including the N-terminal amino group may be carried out by conventional and well-known techniques. For example, by reacting the hydroxyl, amino or imino groups of the compounds (I) with an acylating agent such as an acyl halide of the formula:

(XI)

wherein Z represents halogen such as chlorine, bromine and iodine and

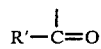

is a carboxylic acid acyl radical, advantageously a hydrocarbon carboxylic acid acyl of not more than 18 carbon atoms; or a halo-, nitro-, hydroxy-, amino-, cyano-, thiocyano-, or lower alkoxy- substituted hydrocarbon carboxylic acid acyl radical advantageously of not more than 18 carbon atoms. Representative of carboxylic acid acyl radicals are the acyl radicals of the following acids:

(a) saturated or unsaturated, straight or branched chain aliphatic carboxylic acids, for example acetic, propionic, butyric, isobutyric, tert-butylacetic, valeric, isovaleric, caproic, caprylic, succinic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, methylcyclopentenecarboxylic acid, cyclohexanecarboxylic acid, dimethylcyclohexenecarboxylic acid, dipropylcyclohexanecarboxylic acid, and the like; (c) saturated or unsaturated, alicyclic aliphatic carboxylic acids, for example cyclopentanepropionic acid cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid, phenylpropionic acid and naphthylacetic acid, and the like. Suitable halo-, nitro-, hydroxy-, amino-, cyano-, thio-, cyano-, and lower alkoxyhydrocarbon carboxylic acids include hydrocarbon carboxylic acids as given above which are substituted by one or more of halogen, nitro, hydroxy, amino, cyano, or thiocyano, or loweralkoxy, advantageously lower-alkoxy of not more than 18 carbon atoms, for example, methoxy, ethoxy, propoxy, butoxy, amyloxy, hexyloxy, and isomeric forms thereof. Examples of such substituted hydrocarbon carboxylic acids are mono, di-, and trichloracetic acid;
α and β-chloropropionic acid
α and γ-bromobutyric acid;
α and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
6-bromo-2-methylcyclohexanecarboxylic acid;
2,3-dibromo-2-methyl-cyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
salicylic acid;
p-hydroxybenzoic acid;
β-resorcyclic acid;
gallic acid;
veratric acid;
2,4,6-trimethoxybenzoic acid;
2,4,6-trimethoxycinnamic acid;
4,4'-dichlorobenzilic acid
o-, m-, and p-nitrobenzoic acid;
cyanoacetic acid;
3,4- and 3,5-dinitrobenzoic acid;
2,4,6-trinitrobenzoic acid;
thiocyanoacetic acid;
1-cyanopropionic acid;
lactic acid;
ethoxyformic acid (ethyl hydrogen carbonate);
butyloxyformic acid;
pentyloxyformic acid;
hexyloxyformic acid;

dodecyloxyformic acid;
hexadecyloxyformic acid; and the like.

Alternatively the acid anhydrides, where available, may be used to acylate the compounds (I) of the invention.

The acylation is advantageously carried out by admixture of the acylating halide or anhyride with the compound (I) in the presence of an acid binding agent, for example a tertiary amine. Illustrative of tertiary amines which may be used are pyridine, quinoline, trimethylamine, triethylamine and the like. Advantageously the acylation is carried out in the presence of an inert solvent, i.e.; a solvent for the acylating agent which does not interfere with or alter the desired course of the acylation. Representative of such inert solvents are chloroform, diethyl ether, dimethylformamide and the like.

Also within the scope of the invention are the ester derivatives of the compounds (I) obtained by reaction of an alcohol with the C-terminal carboxyl group of the compounds (I) of the invention, i.e.; for example a compound of the formula:

$$H+A)+(B)_{\overline{X}}O-R'' \qquad (XII)$$

wherein A, B and X are as previously defined and R'' is the residue of an alcohol. The esterification may be carried out by conventional and known procedures well known to those skilled in the art.

In general, the esterification comprises the reaction of an alcohol with the compound (I) after protection of amine groups with a protective group removable by hydrogenolysis. Following esterification, the protective group is removed to obtain the desired ester.

Representative of alcohols which may be used to obtain the desired ester derivative are lower alkanols such as methanol, ethanol, n-propanol, isopropanol, n-butanol, sec-butanol, t-butanol, p-pentanol, hexanol and the like; aralkanols such as benzyl or benzhydryl alcohol and the like; substituted aralkanols such as p-nitrobenzyl alcohol, p-methoxybenzyl alcohol, 2,4,6-trimethylbenzyl alcohol and the like.

Preferred alcohols for preparing the esters of the compounds (I) are mono- or polyfunctional alcohols of higher molecular weight such as octanol, decanol, dodecanol, stearyl alcohol, octanediol, ribose, sucrose, sorbitol, glucose, mannitol and the like including isomeric forms thereof.

The novel compounds (I) of the invention and derivatives thereof exist either in the non-protonated (free base) form or in the protonated (acid addition salt) form, depending on the pH of the environment. They form stable protonates, i.e.; acid addition salts, on neutralization of the free base with suitable acids. Salts of the compounds (I) are made by neutralizing the free base with the appropriate acid to below about pH 7.0 and advantageously to about pH 2 to pH 6. Suitable acids for this purpose include hydrochloric, sulfuric, phosphoric, thiocyanic, glucosilicic, acetic, succinic, citric, lactic, maleic, fumaric, pamoic, cholic, palmitic, mucic, camphoric, glutaric, glycolic, phthalic, tartaric, lauric, stearic, salicylic, 3-phenylsalicyclic, 5-phenylsalicyclic, 3-methylglutaric, orthosulfobenzoic, cyclohexanesulfamic, cyclopentanepropionic, 1,3-cyclohexanedicarboxylic, 4-cyclohexanecarboxylic, octadecenylsuccinic, octenylsuccinic, methanesulfonic, benzenesulfonic, helianthic, Reinecke's, azobenzenesulfonic, octadecylsulfuric, picric and like acids. Conversely, the free base of compounds (I) are obtained from the corresponding salt, for example from the hydrochloric or sulfate salt, by dissolving or suspending the salt in buffer at about pH 5 to 7, preferably about pH 6, extracting with an immiscible organic solvent, for example chloroform, drying the extract, for example with anhydrous sodium sulfate, and removing the solvent by evaporation.

Acid addition salts of the compounds (I) of this invention may be used to upgrade the free bases, namely, by making acid addition salts of the free bases, subjecting them to purification procedures and then converting the salts back to the free bases by neutralizing with an alkali or contacting with an anionic resin, advantageously to about pH 7.5 to 8.5.

The pharmaceutically acceptable acid addition salts may be used for the same purposes as the free base. Illustrative of pharmaceutically acceptable acid addition salts are those formed upon reaction of the compounds (I) with hydrochloric acid, hydrobromic acid, sulfuric acid, phosphoric acid, acetic acid, lactic acid, citric acid, succinic acid, benzoic acid, salicylic acid, pamoic acid, cyclohexanesulfamic acid and the like.

The following examples describe the manner and process of making and using the invention and set forth the best mode contemplated by the inventor of carrying out the invention, but are not to be construed as limiting.

PREPARATION 1

The blocked or t-butyloxycarbonyl amino acids (referred to hereinafter for convenience as t-Boc amino acid) used in the preparation of the compounds (I) of the invention may be purchased commercially or they may be prepared according to the method of Schwyzer et al., Helv. Chem. Acts., 42, 2622, (1959). Similarly, the t-Boc- amino acids-resin esters are available commercially or they may be prepared according to the procedure of Merrifield, supra.

EXAMPLE 1

(A)

A suitable reaction vessel is charged with 2.0 gms. of cross linked polyvinyl chloride resin containing from 0.25 to 0.5 moles of glycine per gram (Boc-glycine-resin ester, Peninsula Laboratories, Inc., San Carlos, CA). The vessel is then vented and repeatedly pressured with nitrogen gas to remove all traces of air from the reaction vessel. The vent is then closed to maintain a nitrogen gas atmosphere in the reaction vessel.

(B) Deblocking the Starting Boc-Glycine Resin Ester

While maintaining the nitrogen gas atmosphere, there is added to the charged vessel of step (A) above, with stirring 15-25 ml. of a mixture of trifluoroacetic acid, methylene chloride and 2-mercaptoethanol (50:45:5:V/V/V). The resulting mixture is stirred for about 21 minutes, washed successively with methylene chloride, dioxane and then diluted with 20 ml of 5.5 N solution of hydrochloric acid in dioxane. The mixture is then shaken for about 15 minutes, and filtered. The residue is washed successively with dioxane, chloroform and then neutralized with 10 to 12% by weight triethylamine in chloroform, washed with chloroform, then methylene chloride or dimethylformamide depending on the next solvent to be used.

(C) L-lysine Coupling

While maintaining the nitrogen gas atmosphere, three fold molar excess of resin capacity of benzyl-Boc-L-lysine [Lys (Z), Peninsula, supra.] dissolved in methylene chloride is added to the residue of step (B) above. The resulting mixture is shaken and after about 10 minutes, 3 fold molar excess of N,N-dicyclohexylcarbodiimide dissolved in 10–15 ml. of methylene chloride is added with stirring. The resulting mixture is shaken at room temperature for 4.5 to 5 hours. At the end of this period, the reaction mixture is filtered and the residue washed with methylene chloride, ethanol and dried.

(D) Deblocking of the Product of Step (C)

While maintaining the nitrogen atmosphere, the product of Step (C) is deblocked following the procedure of Step (B) above to obtain the product of formula:

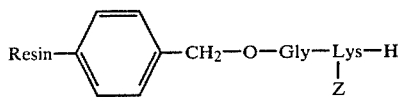

where Z is the protective benzyl oxycarbonyl group.

(E) Coupling of Glutamine

To the product of Step (D) above there is added with mixing 4 molar excess of the p-nitrophenyl ester of Boc-L-glutamine [Gln (ON$_p$), Peninsula, supra.] dissolved in 15–20 ml. of dimethylformamide containing 1.5 M urea. The resulting mixture is shaken overnight, filtered, washed with dimethylformamide-ethanol mixture and dried.

(F) Deblocking of the Product of Step (E)

While maintaining the nitrogen atmosphere, the product of Step (F) above is deblocked following the procedure of Step (B) above to obtain a product of formula:

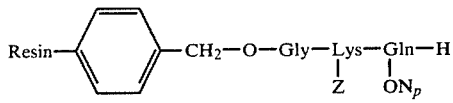

wherein Z is as previously defined and ON$_p$ represents the protective p-nitrophenyl ester group.

(G) Coupling of Tryptophan

While maintaining the nitrogen gas atmosphere, 3 fold molar excess of Boc-L-Tryptophan (Peninsula, supra.) dissolved in dimethylformamide and adjusted to 15 ml. with the addition of methylene chloride is added to the product of Step (F) above and the resulting mixture shaken. After about 10 minutes, 3 fold molar excess of N,N-dicyclohexylcarbodiimide is added and the resulting mixture is shaken for 4.5 to 5 hours at room temperature. At the end of this period, the reaction mixture is filtered and the residue washed with dimethylformamide. The washed residue is dried.

(H) Deblocking the Product of Step (G)

While maintaining the nitrogen atmosphere, the product of Step (G) is deblocked following the procedure of Step (B) above to obtain the product of formula:

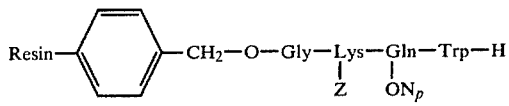

where Z and ON$_p$ are as before defined.

(I) Coupling of Serine

While maintaining the nitrogen gas atmosphere, 3 fold molar excess of the benzyl ester of Boc-L-serine [Boc-L-Ser (OBzl), Peninsula, supra] dissolved in 15 ml of methylene chloride is added to the residue of Step (H) above. The resulting mixture is shaken and after about 10 minutes, 3 fold molar excess of N,N-dicyclohexylcarbodiimide in 15–20 ml. of methylene chloride is added with stirring. The resulting mixture is shaken at room temperature for 4.5 to 5 hours. At the end of this period, the reaction mixture is filtered and the residue washed and dried.

(J) Deblocking of the Product of Step (I)

While maintaining the nitrogen atmosphere, the product of Step (I) above is deblocked following the procedure of Step (B) above to obtain a product of formula :

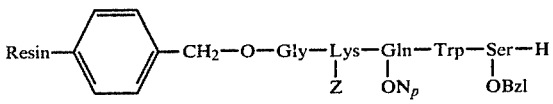

wherein Z and ON$_p$ are as previously defined; OBzl is a benzyloxy protective group.

(K) Coupling of Phenylalanine

While maintaining the nitrogen atmosphere, the product of Step (J) above is admixed with 3 fold molar excess of carbobenzoxy-L-phenylalanine [Boc-L-phenylalanine, Peninsula, supra.] dissolved in methylene chloride. The resulting mixture is shaken and after about 10 minutes, 3 fold molar excess of N,N-dicyclohexylcarbodiimide in 15 ml of methylene chloride is added with stirring. The resulting mixture is shaken at room temperature for 4.5 to 5 hours. At the end of this period, the reaction mixture is filtered and the residue washed and dried.

(L) Deblocking of the Product of Step (K)

While maintaining the nitrogen atmosphere, the product of Step (K) above is deblocked following the procedure of Step (B) above to obtain a product of formula:

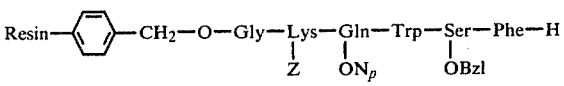

wherein Z, ON$_p$ and OBzl are as before defined.

(M)

The above Steps C-L, inclusive, are repeated sequentially three additional times to obtain the product of formula:

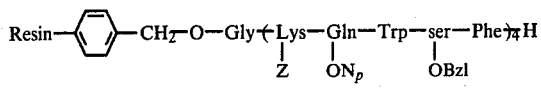

(N)

The product of Step M above is admixed with 10 ml of dry hydrogen fluoride for 1 hour at a temperature of 0° C. in the presence of 1 ml. of anisole. At the end of this period, the residue is separated from the hydrogen fluoride, washed, several times with diethyl ether and then dried. The remaining residue is extracted with trifluorocetic acid and the extract neutralized with 5% by weight sodium bicarbonate. The neutralized residue is then chromatographed on a column of Sephadex G–10 (3×100 cm). The column is equiliberated and the desired product eluted with 0.1 M acetic acid [method of Hashim et al., Biochem. Biophys. Res. Commun., 50,589, (1973a); Arch. Biochem. Biophys., 156, 287, (1973b)]. The product obtained is of the formula:

The purity of the product is established by chromatography and high voltage and polyacrylamide disc gel electrophoresis (method of Hashim et al., Archs. Biochem. Biophys., 129, 635–44, (1969). Amino acid analysis gives whole integers of expected residues.

EXAMPLE 2

(A)

A suitable reaction vessel is charged with 100 gms of carbo-t-butyloxy-L-lysine polymer containing from 0.25 to 0.5 moles of L-lysine per gram [Boc-L-lysine(Z)-resin ester, Peninsula, supra.]. The vessel is then vented and repeatedly pressured with nitrogen gas to remove all traces of air from the reaction vessel. The vent is then closed to maintain a nitrogen gas atmosphere in the reaction vessel.

(B) Deblocking the Starting Boc-L-lysine Resin Ester

The Boc-L-lysine resin ester charge of Step (A) above is deblocked following the procedure of Step (B), Example 1, supra.

(C) Coupling of Glutamine

To the product of Step (B) above, the P-nitrophenyl ester of Boc-L-Glutamine [Gln (ON$_p$), Peninsula, supra.] is coupled following the procedure of Step (E), Example 1, supra.

(D) Deblocking of the Product of Step (C)

The procedure of Step (B), Example 1, supra., is followed to obtain the product of formula:

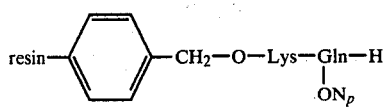

where ON$_p$ represents the protective p-nitrophenyl group.

(E) Coupling of Glycine

The product of Step (D) above is reacted with Boc-glycine according to the procedure of Step C, Example 1, above, and the product thereof deblocked according to Step B of Example 1, supra. to obtain a product of formula:

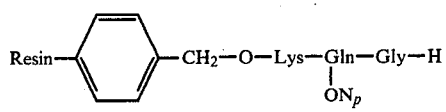

(F)

The procedure of Step E above is repeated 3 additional times to obtain a product of formula:

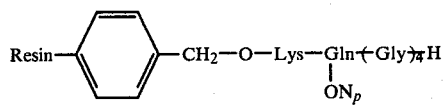

(G) Coupling of Tryptophan

L-tryptophan is coupled to the product of Step (F) above, following the procedure of Step (G), Example 1, supra. The product is deblocked to obtain a product of formula:

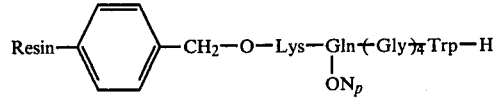

(H)

Step (E) above is repeated twice, starting with the product of Step (G) above, to obtain a product of formula:

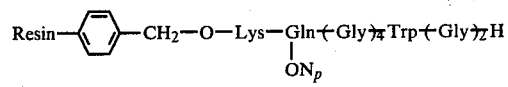

(I)

The product of Step (H) above is treated according to the procedure of Step (N), Example 1, supra to obtain a final product of formula:

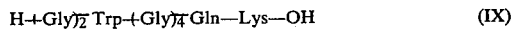

(IX)

EXAMPLE 3

(A)

A suitable reaction vessel is charged with 2.0 gms. of cross linked polyvinyl chloride resin containing from 0.25 to 0.5 moles of glycine per gram (Boc-glycine resin ester, Peninsula Laboratories, Inc., San Carlos, CA). The vessel is then vented and repeatedly pressured with nitrogen gas to remove all traces of air from the reaction vessel. The vent is then closed to maintain a nitrogen gas atmosphere in the reaction vessel.

(B) Deblocking the Starting Boc-glycine Resin Ester

While maintaining the nitrogen gas atmosphere, there is added to the charged vessel of step (A) above, with stirring 15-25 ml. of a mixture of trifluoroacetic acid, methylene chloride and mercaptoethanol (50:45:5:V//V). The resulting mixture is stirred for about 21 minutes, washed successively with methylene chloride, dioxane and then diluted with 20 ml. of 5.5 N solution of hydrochloric acid in dioxane. The mixture is then shaken for about 15 minutes, and filtered. The residue is washed successively with dioxane, chloroform and then neutralized with 10 to 12% by weight triethylamine in chloroform, washed with chloroform, then dimethylformamide.

(C) Coupling of Tryptophan

While maintaining the nitrogen gas atmosphere, 3 fold molar excess of Boc-L-Tryptophan (Peninsula, supra.) dissolved in dimethylformamide and adjusted to 15 ml. with the addition of methylene chloride is added to the product of the previous step above and the resulting mixture shaken. After about 10 minutes, 3 fold molar excess of N,N-dicyclohexylcarbodiimide is added and the resulting mixture is shaken for 4.5 to 5 hours at room temperature. At the end of this period, the reaction mixture is filtered and the residue washed with dimethylformamide. The washed residue is dried.

(D) Deblocking the Product of Step (C)

While maintaining the nitrogen atmosphere, the product of Step (C) is deblocked following the procedure of Step (B) above to obtain the product of formula:

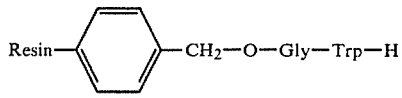

(E) L-lysine Coupling

While maintaining the nitrogen gas atmosphere, three fold molar excess of resin capacity of benzyl-Boc-L-lysine [Lus (Z), Peninsula, supra.] dissolved in methylene chloride is added to the residue of Step (D) above. The resulting mixture is shaken and after about 10 minutes, 3 fold molar excess of N,N-dicyclohexylcarbodiimide dissolved in 10-15 ml. of methylene chloride is added with stirring. The resulting mixture is shaken at room temperature for 4.5 to 5 hours. At the end of this period, the reaction mixture is filtered and the residue washed with methylene chloride, ethanol and dried.

(F) Deblocking of the Product of Step (E)

While maintaining the nitrogen atmosphere, the product of Step (E) is deblocked following the procedure of Step (B) above to obtain the product of formula:

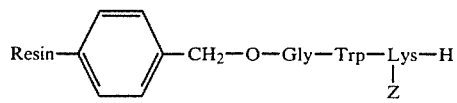

where Z is the protective benzyl group.

(G) Coupling of Glutamine

To the product of Step (F) above there is added with mixing 4 molar excess of the p-nitrophenyl ester of Boc-L-glutamine [Gln (ON$_p$), Peninsula, supra.] dissolved in 15-20 ml. of dimethylformamide containing 1.5 M urea. The resulting mixture is shaken overnight, filtered, washed with dimethylformamide-ethanol mixture and dried.

(H) Deblocking of the Product of Step (G)

While maintaining the nitrogen atmosphere, the product of Step (G) above is deblocked following the procedure of Step (B) above to obtain a product of formula:

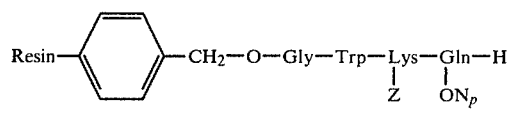

wherein Z is as previously defined and ON$_p$ represents the protective p-nitrophenyl ester group.

(I)

Repeating the Steps (E) and (F) above, on the product of Step (H), there is obtained a product of the formula:

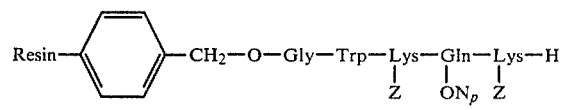

wherein Z and ON$_p$ are as previously defined.

(J) Coupling of Serine

While maintaining the nitrogen gas atmosphere, 3 fold molar excess of the benzyl ester of Boc-L-serine [Boc-L-Ser (OBzl), Peninsula, supra.] dissolved in 15 ml. of methylene chloride is added to the residue of Step (I) above. The resulting mixture is shaken and after about 10 minutes, 3 fold molar excess of N,N-dicyclohexylcarbodiimide in 15-20 ml. of methylene chloride is added with stirring. The resulting mixture is shaken at room temperature for 4.5 to 5 hours. At the end of this period, the reaction mixture is filtered and the residue washed and dried.

(K) Deblocking of the Product of Step (J)

While maintaining the nitrogen atmosphere, the product of Step (J) above is deblocked following the procedure of Step (B) above to obtain a product of formula:

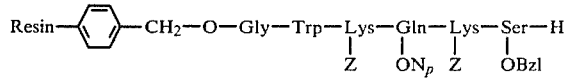

wherein Z and ON$_p$ are as previously defined; OBzl is the benzyloxy protective group.

(L) Coupling of Phenylalanine

While maintaining the nitrogen atmosphere, the product of Step (K) above is admixed with 3 fold molar excess of carbobenzoxy-L-phenylalanine [Boc-L- phenylalanine, Peninsula, supra.] dissolved in methylene chloride. The resulting mixture is shaken and after about 10 minutes, 3 fold molar excess of N,N-dicyclohexylcarbodiimide in 15 ml. of methylene chloride is added with stirring. The resulting mixture is shaken at room temperature for 4.5 to 5 hours. At the end of this period, the reaction mixture is filtered and the residue washed and dried.

(M) Deblocking of the Product of Step (L)

While maintaining the nitrogen atmosphere, the product of Step (L) above is deblocked following the procedure of Step (B) above to obtain a product of formula:

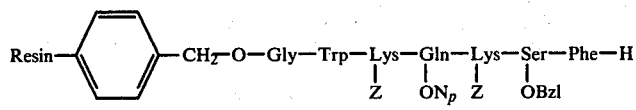

wherein Z, $ON_p$ and OBzl are as before defined.

(N)

The Steps (C)–(K) above are repeated on the product of Step (M), to obtain a product of the formula:

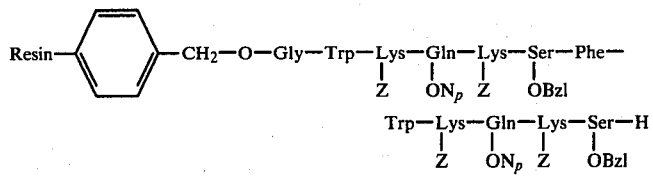

wherein Z, $ON_p$ and OBzl are as defined above.

(O)

The product of Step (N) above is admixed with 10 ml. of dry hydrogen fluoride for 1 hour at a temperature of 0° C. in the presence of 1 ml. of anisole. At the end of this period, the residue is separated from the hydrogen fluoride, washed several times with ether and then dried. The remaining residue is extracted with trifluorocetic acid and the extract neutralized with 5% sodium bicarbonate. The neutralized residue is then chromatographed on a column of Sephadex G-10 (3×100 cm). The column is equilibrated and the desired product eluted with 0.1 M acetic acid [method of Hashim et al., Biochem, Biophys. Res. Commun., 50,589, (1973a); Arch. Biochem. Bioplys., 156, 287, (1973b)]. The product obtained is of the formula:

HO—Gly—Trp—Lys—Gln—Lys—Ser—Phe—Trp—Lys—Gln—Lys—Ser—H (XIII)

The purity of the product is established by chromatography and high voltage and polyacrylamide disc gel electrophoresis (method of Hashim et al., Archs. Biochem. Biophys., 129, 635–44, (1969). Amino acid analysis gives whole integers of expected residues.

EXAMPLE 4

Following the procedure of Example 3, supra., but inserting the following Steps B-1 through B-4 between Steps (B) and (C) as carried out therein, and repeating the Steps B-1 through B-4 again between Steps (N) and (O), a product is obtained having the structural formula:

HO—Gly—Phe—Ser—Trp—Lys—Gln—Lys—Ser—Phe—Trp—Lys—Gln—Lys—Ser—Phe—Ser—H (XIV)

(B-1) Coupling of Phenylalanine

While maintaining the nitrogen atmosphere, the product of Step (B) above is admixed wiht 3 fold molar excess of carbobenzoxy-L-phenylalanine [Boc-L-phenylalanine, Peninsula, supra.] dissolved in methylene chloride. The resulting mixture is shaken and after about 10 minutes, 3 fold molar excess of N,N-dicyclohexylcarbodiimide in 15 ml. of methylene chloride is added with stirring. The resulting mixture is shaken at room temperature for 4.5 to 5 hours. At the end of this period, the reaction mixture is filtered and the residue washed and dried.

(B-2) Deblocking of the Product of Step (B-1)

While maintaining the nitrogen atmosphere, the product of Step (B-1) above is deblocked following the procedure of Step (B).

(B-3) Coupling of Serine

While maintaining the nitrogen gas atmosphere, 3 fold molar excess of the benzyl ester of Boc-L-serine [Boc-L-Ser (OBzl), Peninsula, supra.] dissolved in 15 ml. of methylene chloride is added to the residue of Step (B-2) above. The resulting mixture is shaken and after about 10 minutes, 3 fold molar excess of N,N-dicyclohexylcarbodiimide in 15–20 ml. of methylene chloride is added with stirring. The resulting mixture is shaken at room temperature for 4.5 to 5 hours. At the end of this period, the reaction mixture is filtered and the residue washed and dried.

(B-4) Deblocking of the Product of Step (B-3)

While maintaining the nitrogen atmosphere, the product of Step (B-3) above is deblocked following the procedure of Step (B).

EXAMPLE 5

Repeating the procedure of Example 3, supra., but replacing the Boc-L-Tryptophan as used in Step (C) with an equal proportion of Boc-O-benzyl-L-Tyrosine, there is obtained a product of the formula:

HO—Gly—Tyr—Lys—Gln—Lys—Ser—Phe—Trp—Lys—Gln—Lys—Ser—H (XV)

EXAMPLE 6

Repeating the procedure of Example 3, supra., but replacing the benzyl-Boc-L-lysine as used in Step (E)

with an equal proportion of Boc-L-Ser (OBzl) there is obtained a product of the formula:

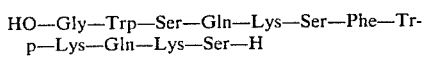
HO—Gly—Trp—Ser—Gln—Lys—Ser—Phe—Trp—Lys—Gln—Lys—Ser—H  (XVI)

EXAMPLE 7

Repeating the procedure of Example 3, supra., but replacing the benzyl-Boc-L-Lysine as used therein in Step (I) with an equal proportion of Boc-L-Arginine, there is obtained a product of the formula:

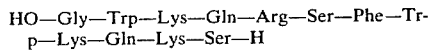
HO—Gly—Trp—Lys—Gln—Arg—Ser—Phe—Trp—Lys—Gln—Lys—Ser—H  (XVII)

EXAMPLE 8

To 25 gms. of the product obtained in Example 3, supra., there is added 5 gms. of the compound of formula:

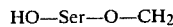
HO—Ser—O—CH$_2$

The mixture is suspended in 100 ml. of dimethylformamide and 450 ml. of acetonitrile. The resulting mixture is stirred for 1 hour at a temperature of 20° C. and then cooled to a temperature of −2° C. The resulting mixture is then admixed with 15 gms. of dicyclohexyl carbodiimide in 50 ml. of acetonitrile and stirred for 6 hours at 0° C. The mixture is allowed to warm to room temperature, filtered and evaporated under reduced pressure. The residue is washed with 5% sodium bicarbonate and water to obtain a product of the formula:

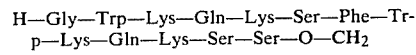
H—Gly—Trp—Lys—Gln—Lys—Ser—Phe—Trp—Lys—Gln—Lys—Ser—Ser—O—CH$_2$  (XVIII)

EXAMPLE 9

The product of Example 3, supra., (25 gms.) is suspended in a mixture of dry ethyl acetate and nitromethane. To the suspension there is added 100 ml. of 6N hydrochloric acid with stirring for 6 hours at room temperature. The mixture is filtered to obtain as a residue the hydrochloric acid salt of the product of Example 3.

EXAMPLE 10

The procedure of Example 1, supra., is repeated except that in Step (A) the polyvinyl chloride resin as used therein is replaced with an equal weight of 1 percent cross-linked polystyrene containing from 0.25 to 0.40 m Moles of t-Boc-E-CBZ-L-lysine (Vega Biochemicals, Tucson, Arizona) and steps (C) and (D) are omitted, Step (E) starting with the product of step (B). The product obtained is of the formula:

H-(-Phe—Ser—Trp—Gln—Lys-)$_x$ OH  (XIX)

Amino acid analysis gives whole integers of the expected residues.

EXAMPLE 11

Repeating the procedure of Example 10, supra., but omitting Steps (M) as described in Example 1, there is obtained a product compound of the formula:

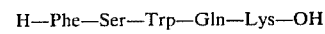
H—Phe—Ser—Trp—Gln—Lys—OH  (XX)

EXAMPLE 12

Steps (A), (B), (E) and (F) as practiced in Example 10, supra., are repeated. The product obtained is treated as follows.

(G) Coupling of Tyrosine

While maintaining the nitrogen gas atmosphere, 3 fold molar excess of Boc-L-Tyrosine (Vega, supra.) dissolved in dimethylformamide and adjusted to 15 ml. with the addition of methylene chloride is added to the product of Step (F) above and the resulting mixture shaken. After about 10 minutes, 3 fold molar excess of N,N-dicyclohexylcarbodiimide is added and the resulting mixture is shaken for 4.5 to 5 hours at room temperature. At the end of this period, the reaction mixture is filtered and the residue washed with dimethylformamide. The washed residue is dried.

(H) Deblocking the Product of Step (G)

While maintaining the nitrogen atmosphere, the product of Step (G) is deblocked following the procedure of Step (B) in Example 10.

(I) Coupling of Histidine

While maintaining the nitrogen gas atmosphere, 3 fold molar excess of the benzyl ester of Boc-L-Histidine (Vega, supra.) dissolved in 15 ml. of methylene chloride is added to the residue of Step (H) above. The resulting mixture is shaken and after about 10 minutes, 3 fold molar excess of N,N-dicyclohexylcarbodiimide in 15-20 ml. of methylene chloride is added with stirring. The resulting mixture is shaken at room temperature for 4.5 to 5 hours. At the end of this period, the reaction mixture is filtered and the residue washed and dried.

(J) Deblocking of the Product of Step (I)

While maintaining the nitrogen atmosphere, the product of Step (I) above is deblocked following the procedure of Step (B) of Example 10.

(K) Coupling of Threonine

While maintaining the nitrogen atmosphere, the product of Step (J) above is admixed with 3 fold molar excess of Boc-L-Threonine, (Vega, supra.,) dissolved in methylene chloride. The resulting mixture is shaken and after about 10 minutes, 3 fold molar excess of N,N-dicyclohexylcarbodiimide in 15 ml. of methylene chloride is added with stirring. The resulting mixture is shaken at room temperature for 4.5 to 5 hours. At the end of this period, the reaction mixture is filtered and the residue washed and dried.

(L) Deblocking of the Product of Step (K)

While maintaining the nitrogen atmosphere, the product of Step (K) above is deblocked following the procedure of Step (B) described in Example 10, supra.

(M)

The above Steps K-L, inclusive, are repeated one additional time.

(N)

The product of Step M above is admixed with 10 ml. of dry hydrogen fluoride for 1 hour at a temperature of 0° C. in the presence of 1 ml. of anisole. At the end of this period, the residue is separated from the hydrogen fluoride, washed several times with diethyl ether and then dried. The remaining residue is extracted with trifluorocetic acid and the extract neutralized with 5% by weight sodium bicarbonate. The neutralized residue is then chromatographed on a column of Sephadex G-10 (3×100 cm). The column is equilibrated and the desired product eluted with 0.1 M acetic acid [method of Hashim et al., Biochem. Biophys. Res. Commun., 50,589, (1973a); Arch. Biochem. Biophys., 156, 287, (1973b)]. The product obtained is of the formula:

$$\text{H—Thr—Thr—His—Tyr—Gln—Lys—OH} \qquad (XXI)$$

The purity of the product is established by chromatography and high voltage and polyacrylamide disc gel electrophoresis (method of Hashim et al., Arch. Biochem. Biophys., 129, 635-44, (1969). Amino acid analysis gives whole integers of expected residues.

EXAMPLE 13

The procedure of Steps (A), (B) and (E) through (M) as practiced in Example 12, supra., is repeated sequentially four times and the product obtained is then treated in accordance with Step (N) of Example 12 to obtain a product of formula:

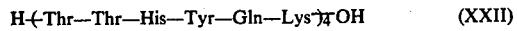 (XXII)

The purity of the product is established by chromatography and high voltage and polyacrylamide disc gel electrophoresis (method of Hashim et al., Archs. Biochem. Biophys., 129, 635-44, (1969). Amino acid analysis gives whole integers of expected residues.

EXAMPLE 14

Steps (A)-(F) inclusive, of Example 1, supra., are repeated in order and the product obtained is treated in accordance with Step (N) of the Example 1 to obtain a product of formula:

$$\text{HO—Gly—Lys—Gln—H} \qquad (XXIII)$$

All of the products of Examples 3-14 above have the biological activity associated with the compounds of formula (V) and (IX) previously described and may be used as described in U.S. Pat. No. 4,113,858 to diagnose, prevent and suppress multiple sclerosis in mammals.

From the foregoing examples, it will be obvious to those skilled in the art that compounds of the invention may be prepared by selection of the appropriate sequence of reactions, employing the known blocked or amino function protected amino acids and the well-known starting amino acid resin esters. Thus, the foregoing general procedure of Examples 1-14 are followed, employing the appropriate Boc-amino acids, to obtain the following additional compounds, representative of those of the formula (I) given above.

H—Gln—Lys—OH;

H—Gln—Arg—OH;

H—Trp—Gln—Lys—OH;

H—Gly—Gln—Lys—OH;

H—Gly—Trp—Gln—Lys—OH;

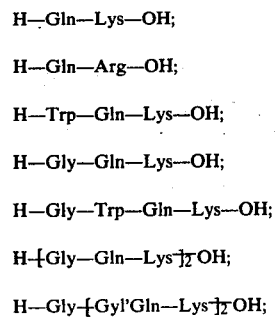

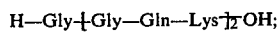

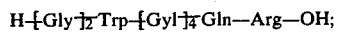

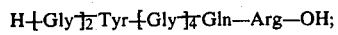

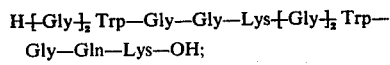

and the like.

Albumin, gamma globulin and like polypeptides, both synthetic and natural, may be reacted with the —OH group at the C-terminal position of compounds of the above formulae to obtain a greater molecular weight, act as a carrier to prevent accelerated decay and enhance the immune response to the synthetic peptide after it has been administered, and allow the peptide to attach to and block sensitized cells from doing further damage. The method of preparation is that described above. See also Merrifield, supra. Thus, there is obtained those compounds (I) of the invention having the more specific formula:

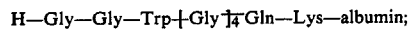

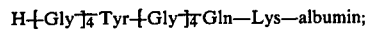

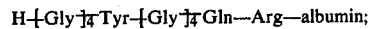

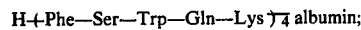

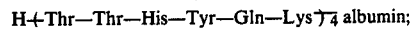

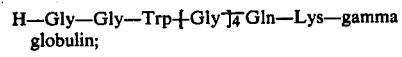

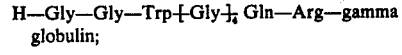

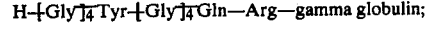

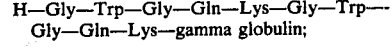

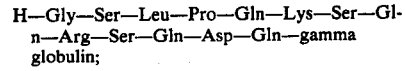

and the like.

When the synthetic compound of formula (I) is in the form of a tripeptide R₂—Gln—R₄ that is where b, c and m in the formula (I-A) are 0, the tripeptide is made following this procedure may be represented as H+Trp—Gln—Lys + OH; H+Trp—Gln—Arg + OH; H+Tyr—Gln—Lys+ OH; and H+Tyr—Gln—Arg+ resulting polypeptide is made following the procedure of Messrs. Hirshmann R., et al, Journal of the American Chemical Society, Vol. 91, p. 507, (1969). Such peptides following this procedure may be represented as H+Trp—Gln—Lys ꝯₙ OH; H—Trp—Gln—Arg ꝯₙ OH; H+Tyr—Gln—Lys ꝯₙ OH; and H+Tyr—Gln—Argꝯₙ OH. When administered to a mammal, these tripeptides prevent cells destined to produce disease, from producing pathologic damage to the nervous tissue in the mammals.

EXAMPLE 15

Parenteral Aqueous Suspension

A sterile aqueous suspension for parenteral administration containing 0.5 mg. of a synthetic compound of formula: H—Phe—Ser—Trp—Gln—Lys$)_{\overline{x}}$ Gly—OH (compound V) in each 1 ml. is prepared from the following types and amounts of ingredients.

| | |
|---|---|
| Compound V, Example 1, supra. | 0.5 gm |
| polysorbate 80 | 8 gms |
| sodium chloride | 18 gms |
| Benzyl alcohol | 18 gms |
| water for injection q.s. | 1000 ml. |

A dose of 1.10 ml. administered subcutaneously to a mammal is useful for diagnosis of multiple sclerosis in multiple sclerosis afflicted mammals; see U.S. Pat. No. 4,113,858. Similarly, repeating the above procedure but replacing the compound V as used therein with an equal weight of any other compound of the invention such as those prepared in Examples 3–14, supra., a therapeutic composition of the invention is obtained.

What is claimed:

1. A synthetic compound selected from those of formula:

$$R_1—Gln—R_4—R_5$$

and the acid addition salts thereof, wherein $R_1$ and $R_5$ are each independently selected from the group consisting of hydrogen, hydroxy, the residue of an amino acid and the residue of a polypeptide and $R_4$ is selected from the group consisting of lysine and arginine residues; provided that $R_1$ and $R_5$ are not both hydrogen or both hydroxyl at the same time.

2. A synthetic compound of claim 1 having the formula:

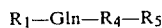

wherein x is an integer of at least 0; A and B each represent a divalent moiety of the formula;

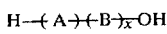

wherein $R_1$ and $R_5$ are each selected from the residue of an amino acid and the residue of a polypeptide; $R_2$ is selected from the residue of tryptophan and tyrosine; $R_3$ represents the residue of an amino acid; $R_4$ is selected from the residue of lysine and arginine; a is an integer of from 0 to 4, inclusive; b and c are each integers of at least 0; m is an integer of from 0 to 1, inclusive; and n is an integer of at least 1; provided that when $R_1$ is the residue of a polypeptide; b is 1 and when $R_5$ is the residue of a polypeptide, c is 1.

3. A compound according to claim 2 wherein said compound has a formula selected from the formulae consisting of:

(a) 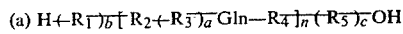

and (b) 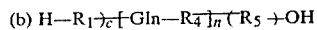

wherein $R_1$, $R_2$, $R_3$, $R_4$, $R_5$, a, b, c and n are as defined in claim 2.

4. A compound according to claim 3 wherein said compound has the formula (a).

5. A compound according to claim 3 wherein said compound has the formula (b).

6. A compound according to claim 4 wherein n is 4.

7. A compound according to claim 5 wherein n is 4.

8. A compound according to claim 2 wherein said compound is of the formula:

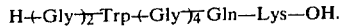

9. A compound of claim 2 wherein said compound is of the formula:

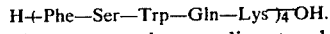

10. A compound according to claim 2 wherein said compound is of the formula:

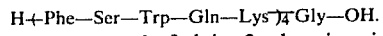

11. A compound of claim 2 wherein said compound is of the formula:

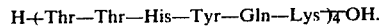

12. The acid addition salt of the compound of claim 2.

13. The pharmaceutically acceptable acid addition salt of the compound of claim 2.

14. The acylate of the compound of claim 2 prepared by acylation of at least one attached group selected from those consisting of hydroxyl, amino and imino, with an acyl halide of the formula:

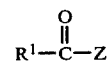

wherein Z represents halogen and the moiety of formula:

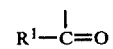

is a carboxylic acid acyl radical.

15. The ester of the compound of claim 2 having the formula:

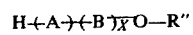

wherein A, B and X are as defined in claim 2 and R″ is the residue of an alcohol selected from the group consisting of mono- and polyfunctional alkanols, aralkanols and substituted aralkanols.

16. A compound according to claim 1 selected from those of the formula selected from the group consisting of

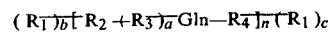

wherein each $R_1$ is a polypeptide having at least a single amino acid residue; $R_2$ is selected from the class consisting of Trp and Tyr; $R_3$ is an amino acid residue; $R_4$ is selected from the class consisting of lysine and arginine; a is 0–4; b and c are each 0 or at least 1 and n is at least 1; and those of the formula:

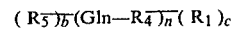

where $R_5$ is selected from the class consisting of $R_1$ and $R_2$ as defined above; and $R_4$, b, c and n are as defined above.

17. A compound according to claim 16 wherein said formula selected is

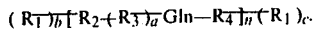

18. A compound according to claim 16 wherein said formula selected is

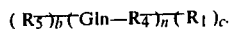

19. The acid addition salt of the compound of claim 16.

20. A compound of claim 16 having the formula:

H—Gly—Gly—Trp—Gly—Gly—Gly—Gly—Gln—Lys—OH.

21. A compound of claim 16 having the formula:

H—Gly—Gly—Trp—Gly—Gly—Gly—Gly—Gln—Arg—OH.

22. A compound of claim 16 having the formula:

H—Gly—Gly—Tyr—Gly—Gly—Gly—Gly—Gln—Lys—OH.

23. A compound of claim 16 having the formula:

H—Gly—Gly—Tyr—Gly—Gly—Gly—Gly—Gln—Arg—OH.

24. A compound of claim 16 having the formula:

25. A compound of claim 16 having the formula:

26. A compound of claim 16 having the formula:

H—Gly—Ser—Leu—Pro—Gln—Lys—Ser—Gln—Arg—Ser—Gln—Asp—Gln—gamma globulin.

27. A pharmaceutical composition, which comprises; an effective amount for the prevention, suppression and diagnosis of multiple sclerosis in mammals of a synthetic compound selected from those of the formula:

$R_1$—Gln—$R_4$—$R_5$ and the pharmaceutically acceptable acid addition salts thereof wherein $R_1$ and $R_5$ are each independently selected from the group consisting of hydrogen, hydroxyl, the residue of an amino acid, and the residue of a polypeptide and $R_4$ is selected from the group consisting of lysine and arginine residues, provided that $R_1$ and $R_5$ are not both hydrogen and are not both hydroxyl at the same time; and a pharmaceutically acceptable parenteral carrier.

28. A pharmaceutical composition according to claim 27 wherein said synthetic compound has the formula:

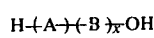

wherein x is an integer of at least 0, A and B each represent a divalent moiety of the formula:

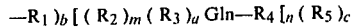

wherein $R_1$ and $R_5$ are each selected from the residue of an amino acid and the residue of a polypeptide; $R_2$ is selected from the residue of tryptophan and tyrosine; $R_3$ represents the residue of an amino acid; $R_4$ is selected from the residue of lysine and arginine; a is an integer of from 0 to 1, inclusive; b and c are each integers of at least 0; m is an integer of from 0 to 1, inclusive; and n is an integer of at least 1; provided that when $R_1$ is the residue of a polypeptide, b is 1 and when $R_5$ is the residue of a polypeptide, c is 1.

* * * * *

UNITED STATES PATENT AND TRADEMARK OFFICE
CERTIFICATE OF CORRECTION

PATENT NO. : 4,230,696                     Page 1 of 2
DATED      : October 28, 1980
INVENTOR(S): George A. Hashim It is certified that error appears in the above—identified patent and that said Letters Patent is hereby corrected as shown below:

Col. 2, line 52, end of formula; - "$(r_5)$" should read -- $(R_5)$ --

Col. 2, line 67; - "and" should read -- that --

Col. 6, line 16; - "hydanoins" should read -- hydantoins --

Col. 6, line 36; - "supression" should read -- suppression --

Col. 9, line 37; - "p-pentanol" should read -- n-pentanol --

Col. 18, line 7; - "wiht" should read -- with --

Col. 21, line 68; - "Gyl'Gln" should read -- Gyl — Gln --

Col. 22, line 56, after the word "following" delete everything to the end of the paragraph and insert in its place -- the procedure of Merrifield supra. When more than one of such tripeptides are linked together, that is, when n of formula (I-A) is greater than 1 the resulting polypeptide is made following the procedure of Messrs. Hirshmann R., et al, Journal of the American Chemical Society, Vol. 91, p. 507, (1969). Such peptides following this procedure may be represented

UNITED STATES PATENT AND TRADEMARK OFFICE
CERTIFICATE OF CORRECTION

PATENT NO. : 4,230,696
DATED : October 28, 1980
INVENTOR(S) : George A. Hashim

It is certified that error appears in the above—identified patent and that said Letters Patent is hereby corrected as shown below:

as $H-[Trp-Gln-Lys]_n-OH$; $H-[Trp-Gln-Arg]_n-OH$; $H-[Tyr-Gln-Lys]_n-OH$; and $H-[Tyr-Gln-Arg]_n-OH$.

When administered to a mammal, these tripeptides prevent cells destined to produce disease, from producing pathologic damage to the nervous tissue in the mammals. --

Signed and Sealed this

Thirteenth Day of October 1981

[SEAL]

Attest:

Attesting Officer

GERALD J. MOSSINGHOFF

Commissioner of Patents and Trademarks